United States Patent [19]
Lang et al.

[11] Patent Number: 5,635,170
[45] Date of Patent: Jun. 3, 1997

[54] COMPOSITION AND METHOD FOR PERMANENT SHAPING OF HAIR

[75] Inventors: Günther Lang, Reinheim; Gerhard Maresch, Darmstadt, both of Germany

[73] Assignee: Wella Aktiengesellschaft, Darmstadt, Germany

[21] Appl. No.: 552,576

[22] Filed: Nov. 3, 1995

[30] Foreign Application Priority Data

Nov. 24, 1994 [DE] Germany ............................ 44 41 873.6

[51] Int. Cl.⁶ .................................................. A61K 7/09
[52] U.S. Cl. ........................................ 424/70.51; 132/210
[58] Field of Search ........................ 424/70.51; 132/210

[56] References Cited

U.S. PATENT DOCUMENTS

| | | | |
|---|---|---|---|
| 4,139,610 | 2/1979 | Miyazaki et al. | 424/72 |
| 4,992,267 | 2/1991 | DenBeste et al. | 424/71 |
| 5,085,860 | 2/1992 | Junino et al. | 424/72 |
| 5,223,252 | 6/1993 | Kolc et al. | 424/72 |
| 5,271,926 | 12/1993 | Kure et al. | 424/71 |
| 5,380,726 | 1/1995 | Ferrini | 514/255 |
| 5,411,991 | 5/1995 | Shander et al. | 514/665 |
| 5,503,826 | 2/1996 | Lang et al. | 424/70.51 |

FOREIGN PATENT DOCUMENTS

| | | |
|---|---|---|
| 0523666 | 1/1993 | European Pat. Off. . |
| 9003780 | 4/1990 | WIPO . |
| 9110421 | 7/1991 | WIPO . |

*Primary Examiner*—Margaret W. Glass
*Attorney, Agent, or Firm*—Michael J. Striker

[57] ABSTRACT

The composition for permanent shaping of hair based on a hair keratin-reducing agent contains N-glycyl-L-cysteine and/or L-cysteinyl-glycine as the hair keratin-reducing agent. The N-glycyl-L-cysteine and/or L-cysteinyl-glycine is advantageously the only hair keratin-reducing substance present. The compositions have a preferred pH range of 6.5 to 9.0 and contain from 8 to 30 percent by weight of the N-glycyl-L-cysteine and/or L-cysteinyl-glycine. Use of this composition for permanent shaping of hair avoids a troublesome white deposit or coating on the hair which occurs when cysteine-containing hair shaping compositions are used.

5 Claims, No Drawings

COMPOSITION AND METHOD FOR PERMANENT SHAPING OF HAIR

BACKGROUND OF THE INVENTION

The present invention relates to a composition and method for permanent shaping of hair based on condensation products of cysteine and glycine.

Weakly acidic to neutral compositions for permanent shaping of hair are advantageously used for careful permanent shaping of damaged, especially white or dyed, hair. During the past 30 years thioglycolic acid esters have proven to be the best reducing agents for this purpose.

There are however a number of disadvantages opposing the advantages provided by a permanent shaping treatment of hair performed with a weakly acidic to neutral permanent shaping composition. Permanent shaping compositions based on thioglycolic acid esters have reduced waveability in comparison to mild alkali shaping agents based on thicoglycolate. For this reason heat, a lengthening of the treatment time to 20 to 60 minutes and the use of comparatively thin curlers are required. Use of this permanent shaping agent for normal, undamaged natural hair is not accepted or meaningful, because of the longer required treatment time of over 30 minutes and the required heat, so that the use of weakly acidic to neutral permanent shaping compositions has up to now usually been limited to pre-damaged, easily worked hair.

An additional considerable disadvantage of acidic permanent shaping compositions is the poor eye and skin compatibility and the sensitizing action of thioglycolic acid esters.

Inspite of a number of attempts the current Sensitizing effects of acidic permanent shaping compositions have not been decisively reduced.

A mildly alkaline (pH=7.1 to 9) permanent shaping composition, which contains cysteine or its salts as active keratin-reducing agents, has been suggested as an alternative.

This hair shaping agent however has a similar series of disadvantages. Cysteine provides only a weak hair shaping effect and has a reduced stability. When cysteine-containing permanent shaping agents are applied to the hair, the cysteine is oxidized quickly by the oxygen in the air to the weakly soluble cystine in water, which forms a difficult-to-remove white coating which is deposited on the hair (so-called "whitening effect").

There have already been a number of attempts to avoid this "whitening effect". They usually include addition of a coreducing agent, or another compound which reduces the oxidizability of cysteine, to hair shaping compositions based on cysteine to solve this problem. The "whitening effect" however could not be eliminated to a satisfactory extent with these steps. Furthermore the current hair shaping compositions including these features have an insufficient hair shaping effect or an unacceptable potential for causing allergic reactions.

SUMMARY OF THE INVENTION

It is an object of the present invention to provide a composition for the permanent shaping of hair which provides a careful and uniform shaping of the hair both under acidic and also weakly alkaline conditions (pH=6.5 to 9.0), but has no or only a slight tendency to cause allergies and forms no troublesome deposit or coating on the hair.

Surprisingly it has been found that a composition for permanent shaping of hair containing N-glycyl-L-cysteine of formula I and/or L-cysteinyl-glycine of formula II:

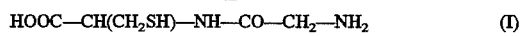

provides a uniform hair shaping and can be used with damaged as well as undamaged hair, without causing the frequently observed allergic skin reactions that have been observed to occur with keratin-reducing ester compounds currently used in hair shaping compositions and without forming the troublesome coating observed with cysteine-containing permanent shaping compositions.

According to the present invention, a particularly advantageous composition for permanent shaping of hair based on an effective keratin-reducing substance contains N-glycyl-L-cysteine (I) and/or L-cysteinyl-glycine as the effective keratin-reducing substance.

Of course it is also possible to use N-glycyl-L-cysteine (I) and/or L-cysteinyl-glycine together with other hair keratin-reducing agents—for example thioglycolic acid, thiolactic acid, 3-hydroxy-2-mercaptopropionic acid, cysteamine and cysteamine derivatives or cysteine and cysteine derivatives, however the use of N-glycyl-L-cysteine (I) and/or L-cysteinyl-glycine alone as the sole keratin-reducing substance (that means without additional keratin-reducing substances or compounds) is particularly preferred and essential to avoid any disadvantages accompanying the use of the other conventional keratin-reducing agent.

The N-glycyl-L-cysteine and/or L-cysteinyl-glycine is used in the ready composition for the permanent shaping of hair according to the invention in an amount of from 8 to 30 percent by weight, advantageously from 10 to 25 percent by weight.

The ready permanent hair shaping composition according to the invention has a pH of from 6.5 to 9.0, advantageously 6.8 to 8.5.

The permanent hair shaping composition can be in the form of an aqueous solution or an emulsion and also in thickened form on an aqueous basis, especially as a gel, cream or paste.

Understandably the permanent shaping composition according to the invention can contain any of the known additive ingredients used in these type of compositions, for example, thickeners, such as kaolin, bentonite, fatty acids, higher fatty alcohols, starches, polyacrylic acids and their derivatives, cellulose derivatives, alginate, VASELINE® (petrolatum) or paraffin oil; wetting agents or emulsifiers selected from the classes of anionic, cationic, amphoteric or nonionic surface active substances, such as fatty alcohol sulfates, fatty alcohol ether sulfates, alkyl sulfonates, alkyl benzene sulfates, quaternary ammonium salts, alkyl betaines, ethoxylated alkylphenols, fatty acid alkanol amides or ethoxylated fatty acid esters; turbidity causing agents, for example polyethylene glycol esters; or alcohols, such as ethanol, propanol, isopropanol or glycerol; solvating agents; stabilizers; buffer substances; perfume oils; dyes and hair conditioning and hair care ingredients, such as cationic polymers, lanolin derivatives, cholesterol, pantothenic acid or betaine. The above-mentioned additive ingredients can be contained in the composition according to the invention in amounts which are standard for that purpose, for example the wetting and emulsifying agents, in a concentration of 0.2 to 30 percent by weight, while the thickening agents, in an amount of 0.5 to 20 percent by weight.

The so-called swelling and penetrating agents, for example dipropyleneglycolmonomethyl ether, 2-pyrrolidone or imidazolidin-2-one, which are often added to improve the effectiveness of compositions of this type, can be added to the composition according to the invention in amounts of 2 to 30 percent by weight. Dithiocompounds, for example dithiodiglycolic acid, dithiodilactic acid or their salts, can also be added to avoid a crossing over or tangling of the hair.

The composition for permanent shaping of hair according to the invention made in the above-described manner is made suitable for any hair type or structure by the variation of pH, if necessary with addition of heat. This composition can be used to provide an elastic, permanent uniform shaping of the hair from the hair roots to hair tips.

The permanent shaping of hair using the composition according to the invention is performed according to the standard method, which includes treating the hair with the composition according to the invention before and/or after bringing it into a predetermined desired shape, rinsing the hair with water, performing an oxidative after-treatment, rinsing with water, putting the hair in a water wave according to the needs of the hair and then drying the hair.

The hair can be washed with a shampoo prior to treatment and after that rinsed with water. Subsequently the hand-towel dried hair is divided into individual strands and wound on curlers with a diameter of from 5 to 30 millimeters, advantageously 5 to 15 millimeters. Then the hair is treated with an effective amount, advantageously from 60 to 120 grams, of the above-described composition according to the invention for permanent shaping of hair.

After a sufficient treatment time for effective permanent shaping of the hair, which, according to the hair condition, the pH value and the shaping effectiveness of the composition and according to the temperature, amounts to from 5 to 30 minutes (10 to 30 minutes without heating but 5 to 20 minutes with heating), the hair is rinsed with water and then oxidatively after-treated ("fixed"). The after-treatment is, according to the hair feel, advantageously used in an amount of 80 to 100 grams.

Any currently known oxidative after-treatment composition can be used for the oxidative after-treatment step according to the invention. Potassium and sodium bromate, sodium perborate, urea peroxide and hydrogen peroxide can, for example, be used in this type of oxidative-aftertreatment composition. The concentration of the oxidizing agent differs depending on the application time (usually 5 to 15 minutes) and the application temperature. Usually the oxidizing agent is present in the ready aqueous after-treatment composition in a concentration of 0.5 to 10 percent by weight. The composition for oxidative after-treatment can contain additional materials, such as wetting agents, hair care materials such as cationic polymers, weak acids, buffer substances or peroxide stabilizers and can be present in the form of an aqueous solution, an emulsion and in thickened form on an aqueous basis, for example as a cream, gel or paste.

Subsequently the curlers are removed. As required, the curled hair can now be after-treated with the oxidative after-treatment composition. Then the hair is rinsed with water, put in a water wave as needed and subsequently dried.

The following examples illustrate the subject matter of the invention.

EXAMPLES OF HAIR SHAPING COMPOSITIONS

Example 1: Permanent Shaping Composition for Dyed Hair

| | |
|---|---|
| 16.0 g | N-glycyl-L-cysteine |
| 3.0 g | copolymer of vinyl pyrrolidone and dimethylaminoethylmethacrylate, quaternarized with diethylsulfate (20% aqueous solution; GAFQUAT ® 755 of GAF Corp., New York, USA) |
| 2.6 g | ammonium hydrogen carbonate |
| 1.5 g | diethyleneglycolmonoethylether |
| 1.5 g | 1,3-butandiol |
| 1.0 g | 1,2-propandiol |
| 1.0 g | cocobetaine |
| 1.0 g | lauryl alcohol, ethoxylated with 4 Mol ethylene oxide |
| 0.8 g | ammonia (25 percent aqueous solution) |
| 0.3 g | vinylpyrrolidone/styrene mixed polymerizate (ANTARA ® of GAF Corp., New York, USA) |
| 0.3 g | perfume oil |
| 71.0 g | water |
| 100.0 | |

The pH of this permanent hair shaping composition amounts to 8.0

Hair mildly damaged by several hair dyeing treatments is washed, rubbed with a hand towel and subsequently the rubbed hair is wound on curlers with a diameter of 8 millimeters. Then the hair wound on the curlers is uniformly moistened with the above-described hair shaping composition. After an acting time of 15 minutes at room temperature the hair is rinsed with water and dried gently with a hand towel. Then the hair wound on the curlers is subjected to an oxidative after-treatment with 80 grams of a 3 percent aqueous hydrogen peroxide solution.

After an acting time of 5 minutes the curlers are removed. After an additional 5 minutes the hair is rinsed with water, rubbed with a hand towel, set in a hair-do and dried.

A uniform elastic permanent shaping of the hair results. Not any white coating remains on the hair.

Example 2: Hair Shaping Composition for Normal Hair

| | |
|---|---|
| 21.4 g | N-glycyl-L-cysteine |
| 5.0 g | ammonium hydrogen carbonate |
| 3.0 g | urea |
| 3.0 g | 1,2-propyleneglycol |
| 1.2 g | ammonia (25 percent aqueous solution) |
| 1.0 g | glycerin-polyethyleneglycol-ricinoleate (CREMOPHOR ® EL of BASF, Ludwigshafen, Germany) |
| 0.6 g | perfume oil |
| 0.5 g | poly (diallyldimethylammonium chloride) |
| 0.2 g | vinyl pyrrolidone/styrene mixed polymerizate (ANTARA ® 430 of GAF Corp., New York, USA) |
| 64.1 g | water |
| 100.0 | |

The pH of this permanent hair shaping composition amounts to 8.5

Normal undamaged hair is washed, rubbed with a hand towel and wound on curlers with a diameter of 6 millimeters.

Subsequently the hair is uniformly moistened with the above-described hair shaping composition. After an acting time of 20 minutes the hair is rinsed with water and then after-treated with 100 grams of a 2.5 percent aqueous hydrogen peroxide solution. After removing the curlers the hair is rinsed again with water, put or set in a water wave and subsequently dried.

The hair thus treated has a uniform and vivacious curl over its entire hair length. Not any white residue is present on the hair.

Example 3: Hair Shaping Composition for Tinted and Blond Hair

| | |
|---|---|
| 12.0 g | L-cysteinyl glycine |
| 2.5 g | monoethanolamine |
| 2.0 g | copolymer of vinyl pyrrolidone and dimethylaminoethylmethacrylate, quaternarized with diethylsulfate (20% aqueous solution; GAFQUAT ® 755 of GAF Corp., New York, USA) |
| 0.8 g | hydrated castor oil, ethoxylated with 45 Mol ethylene oxide (CREMOPHOR ® RH 410 of BASF, Ludwigshafen, Germany) |
| 2.0 g | poly (diallyldimethylammonium chloride) |
| 0.5 g | perfume oil |
| 0.3 g | cocamidopropylbetaine |
| 0.3 g | vinylpyrrolidone/styrene mixed polymerizate (ANTARA ® 430 of GAF Corp., New York, USA) |
| 79.6 g | water |
| 100.0 | |

The pH of this permanent hair shaping composition amounts to 8.8.

The hair is treated in the manner described in Example 1. The acting time of the hair shaping composition however was only 12 minutes and a conventional bromate-containing fixing agent was used for the oxidative after-treatment.

The hair treated in the above-described way was arranged in a uniform curl with locks having a good elasticity and springiness. The deposition of a white coating occurring in cysteine permanent wave treatments was not observed.

All percentages in the above specification are percentages by weight unless otherwise indicated.

While the invention has been illustrated and described as embodied in a composition and method for the permanent shaping of hair, it is not intended to be limited to the details shown, since various modifications and structural changes may be made without departing from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Process for permanent shaping of hair comprising the steps of:

a) putting the hair in a predetermined shape;

b) treating the hair with a hair shaping composition containing at least one of N-glycyl-L-cysteine and L-cysteinyl-glycine as effective hair keratin-reducing agent;

c) rinsing the hair treated in step b) with water;

d) then subjecting the hair to an oxidative after-treatment;

e) rinsing the hair with water, putting the hair in a water wave according the needs of the hair and then drying the hair.

2. Process as defined in claim 1, wherein said hair shaping composition is allowed to act on the hair for from 5 to 30 minutes.

3. Process as defined in claim 1, wherein from 60 to 120 grams of said hair shaping composition are applied to the hair.

4. An aqueous composition for permanent shaping of hair having a pH of 6.5 to 9.0 and containing water; at least one pH-setting and buffering ingredient selected from the group consisting of ammonium hydrogen carbonate, ammonia and monoethanolamine; from 0.2 to 30 percent by weight of at least one additive ingredient and from 8 to 30 percent by weight of at least one keratin-reducing agent selected from the group consisting of N-glycyl-L-cysteine and L-cysteinyl-glycine, wherein said at least one additive ingredient is selected from the group consisting of perfume oils, thickeners, wetting agents, emulsifiers, turbidity causing agents, stabilizers, solvating agents, dyes, hair conditioning ingredients and hair care ingredients.

5. The aqueous composition as defined in claim 4, containing no other keratin-reducing compound besides said at least one keratin-reducing agent selected from the group consisting of N-glycyl-L-cysteine and L-cysteinyl-glycine.

* * * * *